United States Patent [19]

Chinchalkar

[11] Patent Number: 5,643,186
[45] Date of Patent: Jul. 1, 1997

[54] ARCUATE DYNAMIC TRACTION SPLINT

[76] Inventor: Shrikant J. Chinchalkar, 172 Charterhouse Crescent, Ancaster, Ontario, Canada, L9G 4M5

[21] Appl. No.: 531,510

[22] Filed: Sep. 21, 1995

[51] Int. Cl.⁶ .................................................. A61H 1/00
[52] U.S. Cl. .................. 602/32; 602/22; 602/40; 601/40
[58] Field of Search ............... 602/21, 22, 32, 602/36, 37, 39, 40; 606/241; 601/40

[56] References Cited

U.S. PATENT DOCUMENTS

| | | | |
|---|---|---|---|
| 1,949,969 | 3/1934 | Longfellow | 602/37 |
| 2,151,458 | 3/1939 | Allen | 602/32 X |
| 2,646,794 | 10/1953 | Baer | 602/36 X |
| 3,720,206 | 3/1973 | Walker et al. | 602/36 |
| 4,442,452 | 4/1984 | Burton | 602/36 |
| 4,602,620 | 7/1986 | Marx. | |
| 4,644,938 | 2/1987 | Yates et al. | |
| 4,709,916 | 12/1987 | Clark | 601/40 X |
| 4,724,827 | 2/1988 | Schenck | 601/40 |
| 4,765,320 | 8/1988 | Lindemann et al. | |
| 4,809,688 | 3/1989 | Aymerica del Valle et al. | |
| 4,945,902 | 8/1990 | Dorer et al. | 602/36 X |
| 4,949,711 | 8/1990 | Gyovai et al. | |
| 5,413,554 | 5/1995 | Trueman. | |
| 5,446,582 | 8/1995 | Brown | 602/40 X |
| 5,472,407 | 12/1995 | Schenck | 602/22 X |

FOREIGN PATENT DOCUMENTS

| | | | |
|---|---|---|---|
| 2808969 | 9/1979 | Germany | 602/32 |
| 1114413 | 9/1984 | U.S.S.R. | 602/39 |
| 1553118 | 3/1990 | U.S.S.R. | 602/32 |
| 1766400 | 10/1992 | U.S.S.R. | 602/21 |
| 2004219 | 12/1993 | U.S.S.R. | 602/36 |

OTHER PUBLICATIONS

Patel, Distraction Method for Chronic Dorsal Fracture Dislocation of the Proximal Interphalangeal Joint, *Hand Clinics* May 1994, vol. 10, #2, pp. 327–337.

Kearney & Brown, The Therapist's Management of Intra-Articular Fractures, *Hand Clinics* May 1994, vol. 10, #2, pp. 199–209.

*Primary Examiner*—Richard J. Apley
*Assistant Examiner*—David R. Risley

[57] ABSTRACT

An arcuate dynamic traction device for treating a finger having an injured joint, the device being used to apply a distraction force to the injured joint and including a yoke slidably supported on an arcuate track having spaced parallel sides and formed into an arch having a selected radius of curvature. The magnitude of the distraction force applied to the injured joint may be controlled using a tension adjuster that traverses the yoke and which is connected to the injured finger, an adjustable stop engaging the yoke when the desired distraction force is applied. The track is mounted to a forearm splint and can be positioned so that its relative longitudinal position to the forearm and its relative radial position will place the center of the arch on the joint and the finger will move in its normal anatomical plane, in an arcuate path concentric with the arch.

30 Claims, 4 Drawing Sheets

ARCUATE DYNAMIC TRACTION SPLINT

FIELD OF THE INVENTION

This invention relates to a device used to treat a finger injury known in the art as an "intra-articular phalangeal fracture". Such fractures are often complicated by joint compression, due to flexor and extensor tendon axial forces, resulting in fracture malunion. This leads to joint stiffness, tendon adhesions, and pain, sometimes requiring reconstructive surgery and extensive therapy. Such a fracture will be referred to generally in the specification as an "injured joint". Dynamic traction combines the method of traction of the injured joint by the application of a longitudinal distraction force and the method of movement of the finger about the injured joint.

BACKGROUND OF THE INVENTION

Conventional methods of treatment of finger injuries have usually comprised immobilization of the finger, usually by securing the finger to a splint and, in some cases, with the application of a traction force to the distal end of the injured finger to restore congruence at the articular surfaces.

More recently, it has been recognized that the application of both traction and movement is beneficial in the treatment of intra-articular fractures and may achieve articular symmetry with an excellent range of motion without the need for any extensive surgery.

While the method of dynamic traction has been increasingly recognized in the last ten years, there has been no commercially-available apparatus for successfully applying the method. The art teaches the custom fabrication of a splint in which a hoop is fashioned from thermoplastic material and applied to a splint base such that the radius of the circle comprising the hoop is equidistant from the injured joint in all directions when viewed from the side. Rubber bands are threaded through one end of a transosseous wire, passed over the hoop and attached to the wire's other end, with the desired tension being achieved by increasing the number of rubber bands used or by twisting the existing rubber bands. A comprehensive description of the fabrication of such a custom-made splint may be found in the following article "The Therapist's Management of Intra-articular Fractures and Clinics", Volume 10, No. 2 (May 1994), page 199–209.

While clinical test results using the afore-mentioned apparatus are very good, it is the applicant's belief that the dynamic traction method would enjoy more popularity if an apparatus was readily available, in which the time required to prepare the apparatus was minimized. It will be appreciated that hoop alignment to the injured finger's physiological arc of motion is critical to the successful application of the method and that the custom fabrication of every splint is not only time-consuming but inevitably also sometimes unsuccessful because a precise hoop alignment cannot be controlled.

Moreover, the above-described prior art device will allow the phalanges of the articular chain to become misaligned, particularly when the patient performs active assisted exercises on the injured finger and the hoop is not accurately centered on the joint. This may aggravate the injury and prolong the time required for healing.

Applicant has also found that the desired tension in the traction means is preferably adjusted during the course of the treatment so as to maintain congruence at the joint while optimizing the distraction force applied without compromising the vascular supply.

It is an object of this invention to provide suitable apparatus for the application of the dynamic traction method for treating a finger having an injured joint in which at least some of the above-mentioned disadvantages are addressed.

SUMMARY OF THE INVENTION

There is provided a dynamic traction device for treating a finger having an injured joint, the device cooperating with traction means adapted to be secured to the finger between the injured joint and the fingertip and adapted to be placed in tension so as to apply a distraction force to the injured joint.

In accordance with the invention, a yoke slidably supports the traction means on an arcuate track having spaced parallel sides and formed into an arch having a selected radius of curvature.

In accordance with another aspect of the invention, the magnitude of the distraction force applied to the injured joint may be controlled using a tension adjuster that traverses the yoke and supports the traction means, adjustable stop means being provided to engage the yoke when the traction means is placed in tension.

In accordance with yet another aspect of the invention, track securing means are provided to secure the track to the wrist, the track securing means being adapted to adjust the relative longitudinal position of the arcuate track to the forearm and its relative radial position so that the arch may be positioned with the injured joint at the center of the arch such that the finger will pivot about the joint in an arcuate path concentric with the arch. Further adjustability is provided by means adapted to adjust the relative transverse position of the arcuate track to a supporting base so that the arch may be positioned over the injured finger allowing normal anatomical convergence during motion.

BRIEF DESCRIPTION OF THE DRAWINGS

In order that the invention may be more clearly understood, a preferred embodiment is described with reference to the accompanying drawings in which.

DETAILED DESCRIPTION OF THE PREFERRED EMBODIMENT

Figure 1:
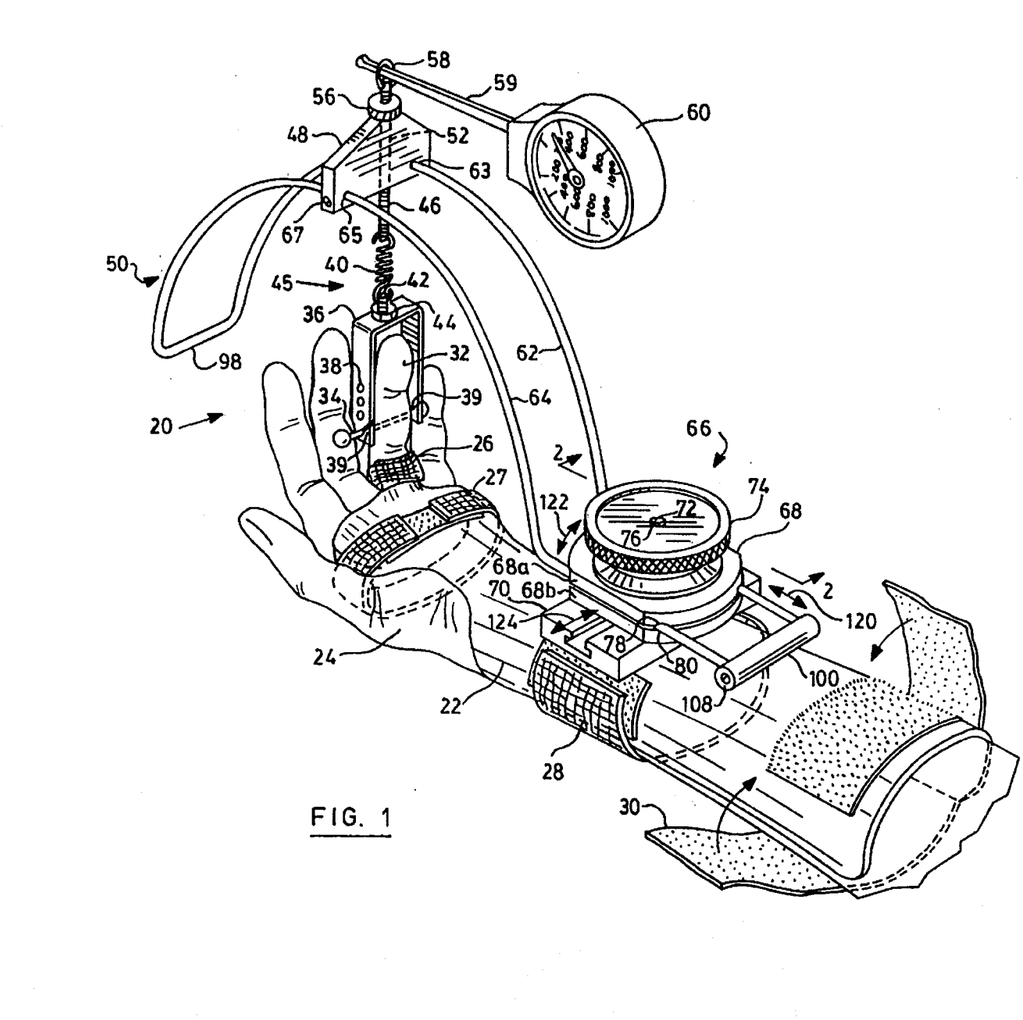
FIG. 1 is a perspective view showing a device made in accordance with the invention, assembled on a forearm and associated with a finger having an injured joint.

A dynamic traction device made in accordance with the invention is generally indicated by numeral 20 in FIG. 1. The device 20 is shown attached to a full forearm splint 22 which is custom-fabricated from a thermoplastic sheet material, as is conventional in the art. The splint 22 extends forwardly from the forearm over the palm of the patient's hand 24 and is anchored to the injured finger by a Velcro™ style hook and loop fastener 26. The extremities of the splint 22 are cut out adjacent the injured finger to allow full mobility of the digits. Additional Velcro™ style fasteners 27, 28, 30 are applied to the hand, the wrist, and the forearm respectively to secure the splint.

In the drawing shown in FIG. 1, the patient has injured the ring finger 32 at the proximal interphalangeal (PIP) joint adjacent the hand. A transosseous K-wire (Kirschnet wire) finger attachment 34 has been surgically inserted through the bone distal to the injured PIP joint. The K-wire 34 extends laterally to either side of the ring finger 32 and a finger clip 36 is mounted to the K-wire 34 where it protrudes from the finger 32.

The finger clip 36 is conveniently fabricated from synthetic plastic material and has a substantially U-shaped configuration with the legs of the U extending on opposite sides of the injured finger. A series of apertures 38 disposed along the length of each leg of the finger clip 36 are provided so that a pair of the apertures matching the height of the K-wire relative to the finger may be selected. A pair of slits 39 are cut to open the selected apertures 38 of the finger clip 36 and to allow the finger clip to be placed on the K-wire 34 while minimizing any additional trauma to the injured joint.

The finger clip 36 forms pan of a joint distracter assembly 45 which, additionally, comprises traction means provided in the form of a coiled spring 40, a tension adjuster and a supporting yoke 48 that supports the joint distracter on an arcuate track generally indicated by numeral 50. The spring 40 is secured at one end to the transverse portion of the U-shaped finger clip adjacent the fingertip by means of a threaded fastener 42 and associated nut 44. The tension adjuster is in the form of a threaded rod 46 that extends through the yoke 48 and is attached to the other end of the coiled spring 40.

The yoke 48 has a through bore 52 which receives the threaded rod 46 and which is dimensioned to exceed the diameter of the rod so that the rod 46 may freely glide through the yoke 48. Stop means in the form of a barrel nut 56 having a knurled outer edge is threaded onto the rod 46 at a selected height, as will be explained in further detail below, and bears against the yoke 48 opposite the finger clip 36. The free ends of the rod 46 are apertured to receive the coiled spring 40 at one end and, on the other end, an annular loop 58, through which the operating arm 59 of a tensiometer 60 may be inserted, as will be explained.

The arcuate track 50 comprises a pair of spaced parallel lengths of rod 62, 64 which have been formed into an arch having a selected radius of curvature, and the yoke 48 has apertures 63, 65 whereby the yoke is adapted to slidingly engage the track. The track radius exceeds the length of the injured finger and will, typically, be 4 ¼ long, with smaller models adapted for use on children having a radius of 3 ½. The arch defined by the rod lengths 62, 64 extends between a distal end spaced from the fingertips and a proximal end adjacent the wrist on the volar side of the forearm.

Track securing means generally indicated by numeral 66 are provided to secure the track 50 to the wrist and include adjustment means to position the track over the injured finger.

Figure 2:
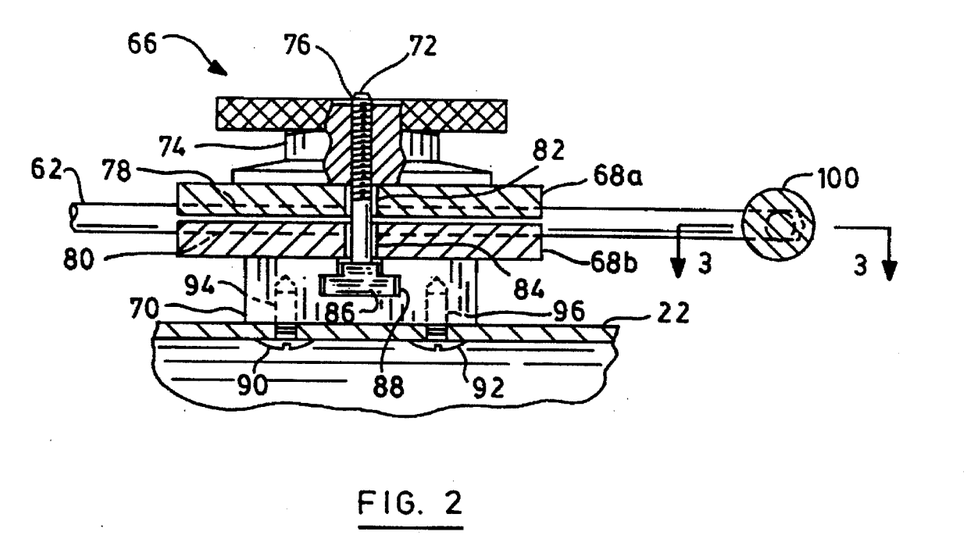
FIG. 2 is a partly-sectioned view drawn on line 2—2 of FIG. 1.

As can be seen more clearly in FIG. 2, the track securing means 66 comprises a track receiving member 68 rotatably mounted to a supporting base 70 on a threaded post 72. The track receiving member 68 is locked to the supporting base 70 by a knob 74 having a central aperture 76 threaded to mate with the post 72. The knob is disposed over the track receiving member 68 so as to sandwich the track receiving member between the knob 74 and the base 70.

The track receiving member 68 is conveniently formed by a pair of congruent plates 68a, 68b disposed one above the other, each having a pair of parallel grooves 78, 80 respectively, and spaced from each other to receive a planar termination of the rod lengths 62, 64. The planar termination is defined at the proximal end of the arch adjacent the wrist where the rods are bent to an obtuse angle in which they define a plane generally parallel to the volar side of the forearm. It will be noted that the cylindrical passages formed by the grooves 78, 80 when the plates 68a and 68b are brought together have an internal diameter which is less than the diameter of the rod lengths 62, 64.

The threaded post 72 traverses the upper and lower plates 68a, 68b of the track receiving member 68 through respective central apertures 82, 84. The post 72 terminates in a slide element 86 having an inverted T-bar cross-section which is slidingly received in a groove 88 of corresponding section provided in the supporting base 70. The supporting base 70 is mounted to the splint 22 by a pair of screw fasteners 90, 92 received in respective threaded holes 94, 96 provided in the supporting base 70. The supporting base 70 is oriented on the splint 22 such that the groove 88 extends across the wrist of the patient transversely to the length of the forearm.

The track securing means 66 is assembled by inserting the planar termination of the rod lengths 62, 64 into the grooved pairs 78, 80 between the upper plate 68a and the lower plate 68b of the track receiving member 68. The knob 74 which bears on the upper plate 68a of the track receiving member is then tightened so that the lower plate 68b of the track receiving member which bears on the upper surface of the supporting base 70 is sandwiched between the base and the upper plate 68a. It will be noted that the depth of the groove 88 traversing the supporting base 70 exceeds the height of the slide element 86 so that the bottom plate 68b of the track receiving member will bear on the operatively upper surface of the supporting base 70.

Figure 3:
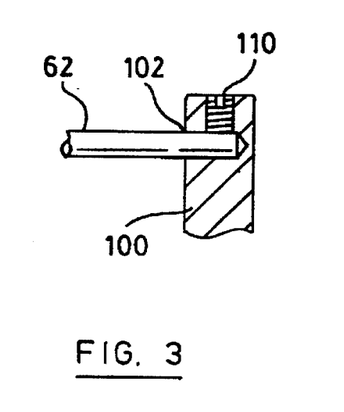
FIG. 3 is a cross-sectional view drawn on line 3—3 of FIG. 2.

The rod lengths 62, 64 are fashioned from one length of rod and are joined at the distal end of the arch by a transverse termination 98 having a length corresponding to the separation between the rod lengths 62, 64. At the free end of the planar termination adjacent the proximal end of the arch, the rod lengths 62, 64 are joined by a transversely disposed cross-bar or stabilizer 100 drawn in the form of a cylinder and shown in more detail in FIG. 3. The cross-bar 100 has a pair of spaced apertures 102, 104 (of which only one is shown in FIG. 3) drilled into the side wall of the cylinder comprising the cross-bar 100 and which are dimensioned to receive respective ends of the rod lengths 62, 64. The length of the cross-bar exceeds the separation between the rod lengths 62, 64 so that set screws 106, 108 inserted into end apertures 110, 112 drilled in the ends of the cylinder will bear upon the free ends of the rod lengths 62, 64 and maintain the rods in a desired angular orientation.

In use, the arcuate track 50 is positioned in the track securing means 66 in accordance with the nature of the injury being treated and the size of the patient's hand. The objective is to center the arch over the injured joint and to guide the injured finger to move in its normal anatomical plane while maintaining alignment of the phalanges of the articular chain of the injured finger.

The planar termination of the rod lengths 62, 64 is extended or retracted as indicated by arrow 120 by adjusting the relative position of the rod lengths to the track receiving member 68, in accordance with the size of the patient's hand and the radial distance separating the injured joint from the planar termination. The arcuate track 50 is then positioned over the injured finger so that the arcuate path followed by a natural bending of the finger about the injured joint will be concentric with the arch defined by the rod lengths 62, 64. This is done by rotating the track receiving member 68 about the post 72 as indicated by arrow 122 so that its radial position relative to the supporting base 70 aligns the track 50 with the injured finger. Thus, the construction of track securing means 66 also recognizes the convergence effect of the fingers of the hand and allows for changes in radial position between one finger and another. Final alignment adjustments may be made by moving the slide element 86 inside the groove 88 as indicated by arrow 124, thereby positioning the track receiving member 68 at the required location on the patient's wrist.

After securing the finger clip 36 to the injured finger, an image intensifier or X-ray machine is used to assess the joint and determine the distraction force needed to counter the finger's tendons and to distract the joint capsule and collateral ligaments for fracture reduction. Typically, a force greater than 200 grams as measured by a Haldex™ gauge tensiometer 60 is applied to the joint. The tensiometer 60 comprises an operating arm 59 which, in use, pivots against a biasing means provided inside a casing. The amount of force required to displace the arm 61 is displayed on a dial in grams and is representative of the distraction force applied to the injured joint. It will be appreciated that an increase in the force of distraction applied to the joint will cause extension of the coiled spring 40 and operate to retract the rod 46 from the associated yoke 48. To maintain the desired position of the rod 46 relative to the yoke 48, the barrel nut 56 is adjusted so as to bear on the yoke.

The distraction force applied to the injured joint is kept constant for a period of about four to six weeks dependent on the progress of the fracture healing.

Daily exercises of the injured joint are performed 15 to 20 times hourly by moving the yoke between predetermined locations on the arcuate track, progressively increasing the range of motion (ROM) of the injured finger as the joint heals. This active assisted exercise is adapted to minimize tendon adhesion formation, to allow free tendon gliding, and healing of the cartilage.

Figure 4:
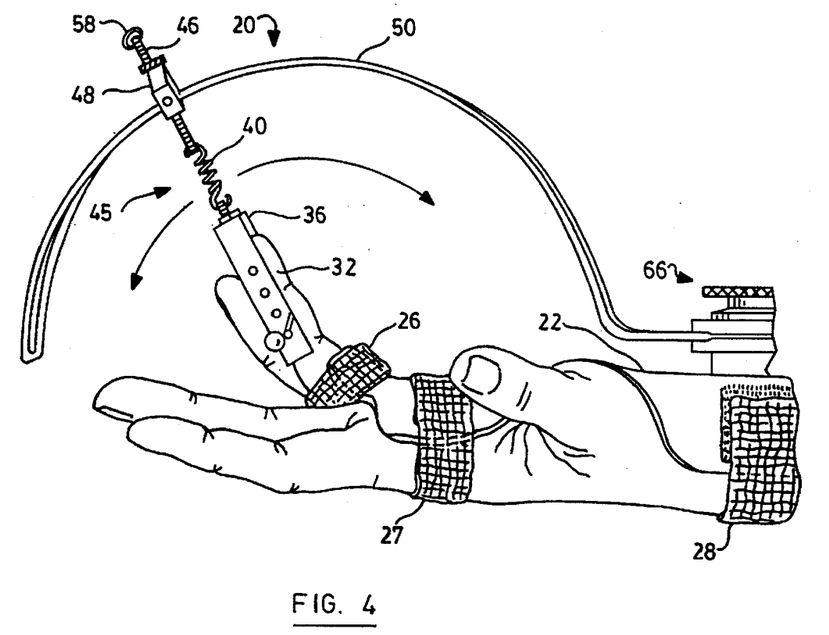
FIGS. 4 and 5 are side views of the device shown in FIG. 1 showing the injured finger in extension and in flexion, respectively.
Figure 5:
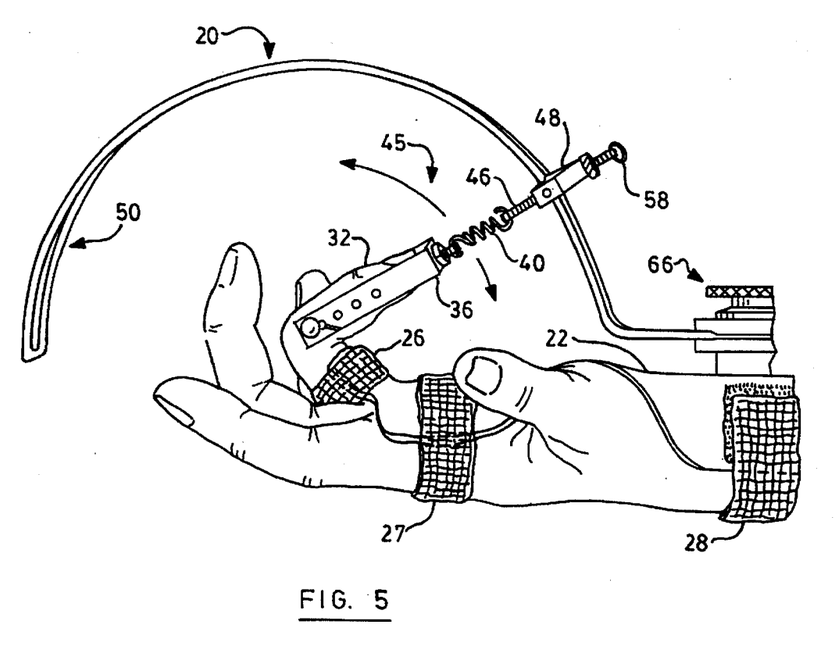

The splint is used continuously for said 4 to 6-week period, during which time the angular displacement of the yoke 48 along the arcuate track 50 is continuously increased between positions in which the finger is extended as shown in FIG. 4 and in which the finger is flexed as shown in FIG. 5 until a maximum range of motion is restored to the injured finger. Meanwhile, a weekly X-ray is performed to ensure that the fracture and joint are satisfactorily reduced. After the dynamic traction apparatus is removed, therapy is maintained.

Experimental work conducted by the Inventor has shown that dynamic traction splinting for intra-articular fractures has a significant effect only if the distraction and movement are performed in an anatomical plane. This is because of the variable length of the collateral ligaments as well as the congruity of the metacarpal and phalangeal condyles. Inventor has found that the convergence of the digits towards the scaphoid that is permitted during motion in an arcuate dynamic traction splint made in accordance with the invention, produces better results than when the method of dynamic traction is applied using more conventional means.

Figure 6:
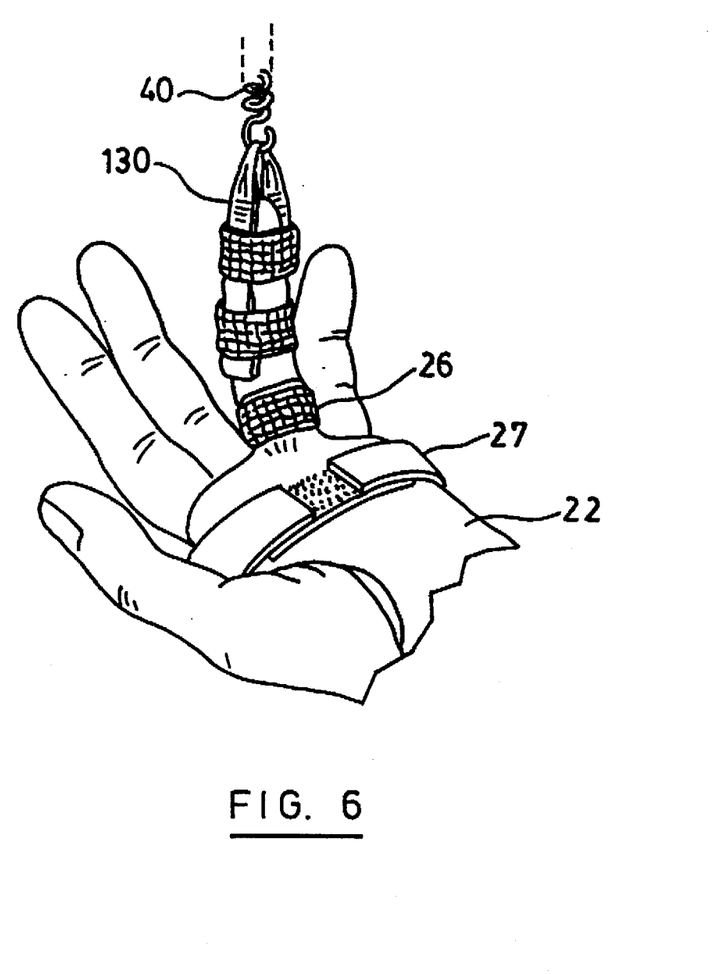
FIG. 6 is a similar view to FIG. 1 showing alternative finger attachment means for use with the invention.

It will be understood that several variations may be made to the above-described embodiment of the invention within the scope of the appended claims. For example, it will be appreciated that the finger attachment means may adopt a number of forms as is well-known in the art. If a small distraction force, e.g. less than 300 grams, is required, the use of a transosseous wire and associated finger clip will not be necessary. A simple nail hook or skin traction bandage 130 (shown in FIG. 6) will be adequate.

While the arcuate track shown has a 180° arc commensurate with the full range of motion (ROM) of a PIP joint, other arcs may be appropriate in certain situations. For example, the normal full range of motion of metacarpal phalangeal joints (MCP) is 90°, in distal interphalangeal joints (DIP), the ROM is 70°, and in the thumb MCP and IP, the ROM is 60°–70°

It will be appreciated that treatment of a joint injury to the thumb would require the apparatus according to the invention to be mounted on the dorsal side of the forearm and the relative angle of the arch to the planar termination to be modified accordingly. Thus it will be understood that general references to fingers in this specification include the thumb as well as the digits of the hand.

It will also be understood that the track securing means may take a number of forms and could, for example, be constructed to provide limited adjustability in a selected range of positions. Thus, the track receiving member 68 could be mounted directly to the splint 22 without a supporting base 70. The track securing means would then simply be attached directly to the splint at the location required to position the arcuate track 50 over the injured finger. A track receiving member could also be fabricated in one piece and locked to the associated splint by other, appropriate means. It is also envisaged that the planar termination of the rod lengths 62, 64 could comprise a plate cooperating with appropriate stops for positioning the arcuate track. Such variations in the structure will be apparent to those skilled in the art.

I claim:

1. A dynamic traction device for treating a finger having an injured joint, and cooperating with traction means adapted to be secured to the finger distal to the injured joint, the traction means having a free end adapted to be placed in tension so as to apply a distraction force to the injured joint, the device comprising:

an arcuate track having a pair of spaced parallel sides formed into an arch having a selected radius of curvature which exceeds the length of the injured finger, and which extends between a free distal end spaced from the fingertip and a proximal end adjacent the associated wrist;

a yoke adapted to support said traction means in tension, the yoke bridging both sides of the track and mounted to the track to slidingly engage the sides of the track so as to be movable along said arch guided by said sides;

a tension adjuster traversing said yoke and adapted for translational movement therethrough, the tension adjuster comprising a threaded rod apertured at one end to receive spring biasing means connected to finger attachment means adapted to be secured to a finger at one end and adapted to apply said distraction force to the injured joint, the tension adjuster having adjustable stop means comprising a barrel nut of corresponding thread disposed on the rod with the yoke between the nut and the finger attachment means, the stop means being adapted to engage the yoke when said distraction force is applied, the relative position of the tension adjuster to the yoke defining the magnitude of the distraction force applied to an injured joint; and track securing means adapted to secure said track to a wrist.

2. Dynamic traction device according to claim 1 in which the other end of the rod is apertured to receive an annular loop through which a tensiometer may be inserted in measure the distraction force applied to an injured joint.

3. Dynamic traction device according to claim 1 in which the arcuate track has a planar termination adjacent said proximal end and the track securing means comprises a track receiving member traversed by said planar termination and adapted to allow translational movement of the planar termination therethrough, the track receiving member being adapted to adjust the relative longitudinal position of the planar termination in the track receiving member and thereby to position the centre of the arch so that it may lie on an injured joint.

4. Dynamic traction device according to claim 3 in which the track receiving member is rotatably mounted to a supporting base and adapted to adjust the relative radial position of the arcuate track to the base and thereby to position the arch so that a finger having an injured joint may pivot about the injured joint in an arcuate path concentric with said arch.

5. Dynamic traction device according to claim 3 in which the track receiving member is slidably mounted for translational movement across the wrist onto a supporting base and adapted to adjust the relative transverse position of the arcuate track to the base and thereby to position the arch over a finger with an injured joint.

6. A dynamic traction device for treating a finger having an injured joint, and cooperating with traction means adapted to be secured to the finger distal to the injured joint, the traction means having a free end adapted to be placed in tension so as to apply a distraction force to the injured joint, the device comprising:

an arcuate tack having a pair of spaced parallel sides formed into an arch having a selected radius of curvature which exceeds the length finger, and which extends between a free distal end spaced from the fingertip and a proximal end adjacent the associated wrist;

a yoke adapted to support said traction means in tension, the yoke bridging both sides of the track and mounted to the track to slidingly engage the sides of the track so as to be movable along said arch guided by said sides;

and track securing means adapted to secure said track to a wrist, the arcuate track having a planar termination adjacent said proximal end and the track securing means comprising a track receiving member traversed by said planar termination and adapted to allow translational movement of the planar termination therethrough in a first direction, the track receiving member having a pair of plates disposed one above the other and adapted to receive and retain said planar termination therebetween, the relative longitudinal position of the planar termination in the track receiving member being infinitely adjustable and thereby adapted to position the centre of the arch so that it may lie on an injured joint.

7. A dynamic traction device for treating a finger having an injured joint, and cooperating with traction means adapted to be secured to the finger distal to the injured joint, the traction means having a free end adapted to be placed in tension so as to apply a distraction force to the injured joint, the device comprising:

an arcuate track having a pair of spaced parallel sides formed into an arch having a selected radius of curvature which exceeds the length of the injured finger, and which extends between a free distal end spaced from the fingertip and a proximal end adjacent the associated wrist;

a yoke adapted to support said traction means in tension, the yoke bridging both sides of the track and mounted to the track to slidingly engage the sides of the track so as to be movable along said arch guided by said sides;

and track securing means adapted to secure said track to a wrist, the arcuate track having a planar termination adjacent said proximal end and the track securing means comprising a track receiving member traversed by said planar termination and adapted to allow translational movement of the planar termination therethrough, the track receiving member being adapted to adjust the relative longitudinal position of the planar termination in the track receiving member and thereby to position the centre of the arch so that it may lie on an injured joint.

8. Dynamic traction device according to claim 7 in which the track receiving member is slidably mounted for translational movement across the wrist onto the supporting base, the base having a groove extending in a second direction transverse to said first direction and adapted to receive and retain one end of said post, the relative transverse position of the arcuate track to the base being infinitely adjustable and thereby adapted to position the arch over a finger with an injured joint.

9. A dynamic traction device for treating a finger having an injured joint, and cooperating with traction means adapted to be secured to the finger distal to the injured joint, the traction means having a free end adapted to be placed in tension so as to apply a distraction force to the injured joint, the device comprising:

an arcuate track having a pair of spaced parallel sides comprising a pair of spaced parallel lengths of rod formed into an arch and having a selected radius of curvature which exceeds the length of the injured finger, and which extends between a free distal end spaced from the fingertip and a proximal end adjacent the associated wrist, a transverse termination formed from said lengths of rod defining said free distal end of the track, and a stabilizer joining free ends of said lengths of rod adjacent to said proximal end, said transverse termination and said stabilizer being adapted to maintain the rod lengths in said spaced parallel orientation;

a yoke adapted to support said traction means in tension, the yoke bridging both sides of the track and mounted to the track to slidingly engage the sides of the track so as to be movable along said arch guided by said sides;

and track securing means adapted to secure said track to a wrist.

10. A dynamic traction device for treating a finger having an injured joint, and cooperating with traction means adapted to be secured to the finger distal to the injured joint, the traction means having a free end adapted to be placed in tension so as to apply a distraction force to the injured joint, the device comprising:

an arcuate track formed into an arch having a selected radius of curvature which exceeds the length of the injured finger, and which extends between a free distal end spaced from the fingertip and a proximal end adjacent the associated wrist;

a yoke adapted to support said traction means in tension, the yoke being mounted to the track and adapted to slidingly engage the sides of the track so as to be movable along said arch;

a tension adjuster traversing said yoke and adapted for translational movement therethrough, the tension adjuster comprising a threaded rod apertured at one end to receive spring biasing means connected to finger attachment means adapted to be secured to a finger at one end and adapted to apply said distraction force to the injured joint, the tension adjuster having adjustable stop means comprising a barrel nut of corresponding thread disposed on the rod with the yoke between the nut and the finger attachment means, the stop means being adapted to engage the yoke when said distraction force is applied, the relative position of the tension adjuster to the yoke defining the magnitude of the distraction force applied to an injured joint, and track securing means adapted to secure said track to a wrist.

11. Dynamic traction device according to claim 10 in which the other end of the rod is apertured to receive an annular loop through which a tensiometer may be inserted to measure the distraction force applied to an injured joint.

12. A dynamic traction device for treating a finger having an injured joint, and cooperating with traction means adapted to be secured to the finger distal to the injured joint, the traction means having a free end adapted to be placed in tension so as to apply a distraction force to fie injured joint, the device comprising:

an arcuate track formed into an arch having a selected radius of curvature which exceeds the length of the injured finger, and which extends between a free distal end spaced from the fingertip and a proximal end adjacent the associated wrist;

a yoke adapted to support said traction means in tension, the yoke being mounted to the track and adapted to slidingly engage the track so as to be movable along said arch;

and track securing means.. adapted to secure said track to a wrist, the arcuate track having a planar termination adjacent said proximal end and the track securing means comprising a track receiving member traversed by said planar termination and adapted to allow translational movement of the planar termination therethrough, the track receiving member being adapted to adjust the relative longitudinal position of the planar termination in the track receiving member and thereby to position the centre of the arch so that it may lie on an injured joint.

13. Dynamic traction device according to claim 12 in which the track receiving member is rotatably mounted to a supporting base and adapted to adjust the relative radial position of the arcuate track to the base and thereby to position the arch so that a finger having an injured joint may pivot about the injured joint in an arcuate path concentric with said arch.

14. Dynamic traction device according to claim 12 in which the track receiving member is slidably mounted for translational movement across the wrist onto a supporting base and adapted to adjust the relative transverse position of the arcuate track to the base and thereby to position the arch over a finger with an injured joint.

15. A dynamic traction device for treating a finger having an injured joint, and cooperating with traction means adapted to be secured to the finger distal to the injured joint, the traction means having a free end adapted to be placed in tension so as to apply a distraction force to the injured joint, the device comprising:

an arcuate track formed into an arch having a selected radius of curvature which exceeds the length of the injured finger, and which extends between a free distal end spaced from the fingertip and a proximal end adjacent the associated wrist;

a yoke adapted to support said traction means in tension, the yoke being mounted to the track and adapted to slidingly engage the track so as to be movable along said arch;

and track securing means adapted to secure said track to a wrist, the arcuate track having a planar termination adjacent said proximal end and the track securing means comprising a track receiving member traversed by said planar termination and adapted to allow translational movement of the planar termination therethrough in a first direction, the track receiving member having a pair of plates disposed one above the other and adapted to receive and retain said planar termination therebetween, the relative longitudinal position of the planar termination in the track receiving member being infinitely adjustable and thereby adapted to position the centre of the arch so that it may lie on an injured joint.

16. Dynamic traction device according to claim 15 in which the track receiving member is rotatably mounted to a supporting base on a post secured to the base at one end and having a free threaded end, a securing nut of corresponding thread being adapted to retain said planar termination of the arcuate track between said plates, the relative radial position of the arcuate track to the base being infinitely adjustable and thereby adapted to position the arch so that a finger having an injured joint may pivot about the injured joint in an arcuate path concentric with said arch.

17. Dynamic traction device according to claim 16 in which the track receiving member is slidably mounted for translational movement across the wrist onto the supporting base, the base having a groove extending in a second direction transverse to said first direction and adapted to receive and retain one end of said post, the relative transverse position of the arcuate track to the base being infinitely adjustable and thereby adapted to position the arch over a finger with an injured joint.

18. A dynamic traction device for treating a finger having an injured joint, and cooperating with traction means adapted to be secured to the finger distal to the injured joint, the traction means having a free end adapted to be placed in tension so as to apply a distraction force to the injured joint, the device comprising:

an arcuate track comprising a pair of spaced parallel lengths of rod formed into an arch and having a selected radius of curvature which exceeds the length of the injured finger, and which extends between a free distal end spaced from the fingertip and a proximal end adjacent the associated wrist, a transverse termination formed from said lengths of rod defining said free distal end of the track, and a stabilizer joining free ends of said lengths of rod adjacent to said proximal end, said transverse termination and said stabilizer being adapted to maintain the rod lengths in said spaced parallel orientation;

a yoke adapted to support said traction means in tension, the yoke being mounted to the track and adapted to slidingly engage the track so as to be movable along said arch;

and track securing means adapted to secure said track to a wrist.

19. A dynamic traction device for treating a finger having an injured joint, and cooperating with traction means adapted to be secured to the finger distal to the injured joint, the traction means having a free end adapted to be placed in tension so as to apply a distraction force to the injured joint, the device comprising:

an arcuate track having a pair of spaced parallel sides formed into an arch having a selected radius of curvature which exceeds the length of the injured finger, and which extends between a free distal end spaced from the fingertip and a proximal end adjacent the associated wrist;

a yoke adapted to support said traction means in tension with the traction means disposed between said parallel sides of the track, the yoke bridging both sides of the track and mounted to the track to slidingly engage the sides of the track so as to be movable along said arch guided by said sides;

a tension adjuster traversing said yoke and adapted for translational movement therethrough, the tension adjuster comprising a threaded rod apertured at one end to receive spring biasing means connected to finger attachment means adapted to be secured to a finger at one end and adapted to apply said distraction force to the injured joint, the tension adjuster having adjustable stop means comprising a barrel nut of corresponding thread disposed on the rod with the yoke between the nut and the finger attachment means, the stop means being adapted to engage the yoke when said distraction force is applied, the relative position of the tension adjuster to the yoke defining the magnitude of the distraction force applied to an injured joint, and the other end of the rod being apertured to receive an annular loop through which a tensiometer may be inserted to measure the distraction force applied to an injured joint; and track securing means adapted to secure said track to a wrist.

20. Dynamic traction device according to claim 19 in which the other end of the rod is apertured to receive an annular loop through which a tensiometer may be inserted to measure the distraction force applied to an injured joint.

21. A dynamic traction device for treating a finger having an injured joint, the device comprising:

an arcuate track having a pair of spaced parallel sides formed into an arch having a selected radius of curvature which exceeds the length of the injured finger, and which extends between a free distal end spaced from the fingertip and a proximal end adjacent the associated wrist;

traction means adapted to be secured to the finger distal to the injured joint, the traction means having a free end adapted to be placed in tension so as to apply a distraction forte to the injured joint;

a yoke adapted to support said traction means in tension with the traction means disposed between said parallel sides of the track, the yoke bridging both sides of the track and mounted to the track to slidingly engage the sides of the track so as to be movable along said arch guided by said sides;

and track securing means adapted to secure said track to a wrist, the arcuate track having a planar termination adjacent said proximal end and the track securing means comprising a track receiving member traversed by said planar termination and adapted to allow translational movement of the planar termination therethrough, the track receiving member being adapted to adjust the relative longitudinal position of the planar termination in the track receiving member and thereby to position fie centre of the arch so that it may lie on an injured joint.

22. Dynamic traction device according to claim 21 in which the track receiving member is rotatably mounted to a supporting base and adapted to adjust the relative radial position of the arcuate track to the base and thereby to position the arch so that a finger having an injured joint may pivot about the injured joint in an arcuate path concentric with said arch.

23. Dynamic traction device according to claim 21 in which the track receiving member is slidably mounted for translational movement across the wrist onto a supporting base and adapted to adjust the relative transverse position of the arcuate track to the base and thereby to position the arch over a finger with an injured joint.

24. A dynamic traction device for treating a finger having an injured joint the device comprising:

an arcuate track having a pair of spaced parallel sides formed into an arch having a selected radius of curvature which exceeds the length of the injured finger, and which extends between a free distal end spaced from the fingertip and a proximal end adjacent the associated wrist;

traction means adapted to be secured to the finger distal to the injured joint, the traction means having a free end adapted to be placed in tension so as to apply a distraction force to the injured joint;

a yoke adapted to support said traction means in tension with the traction means disposed between said parallel sides of the track, the yoke bridging both sides of the track and mounted to the track to slidingly engage the sides of the track so as to be movable along said arch guided by said sides;

and track securing means adapted to secure said track to a wrist the arcuate track having a planar termination adjacent said proximal end and the track securing means comprising a track receiving member traversed by said planar termination and adapted to allow translational movement of the planar termination therethrough in a first direction, the track receiving member having a pair of plates disposed one above the other and adapted to receive and retain said planar termination therebetween, the relative longitudinal position of the planar termination in the track receiving member being infinitely adjustable and thereby adapted to position the centre of the arch so that it may He on an injured joint.

25. Dynamic traction device according to claim 24 in which the track receiving member is rotatably mounted to a supporting base on a post secured to the base at one end and having a free threaded end, a securing nut of corresponding thread being secured to said free threaded end and adapted to retain said planar termination of the arcuate track between said plates, the relative radial position of the arcuate track to the base being infinitely adjustable and thereby adapted to position the arch so that a finger having an injured joint may pivot about the injured joint in an arcuate path concentric with said arch.

26. Dynamic traction device according to claim 25 in which the track receiving member is slidably mounted for translational movement across the wrist onto the supporting base, the base having a groove extending in a second direction transverse to said first direction and adapted to receive and retain one end of said post, the relative transverse position of the arcuate track to the base being infinitely adjustable and thereby adapted to position the arch over a finger with an injured joint.

27. A dynamic traction device for treating a finger having an injured joint, the device comprising;

an arcuate track having a pair of spaced parallel sides comprising a pair of spaced parallel lengths of rod formed into an arch and having a selected radius of curvature which exceeds the length of the injured finger, and which extends between a free distal end spaced from the fingertip and a proximal end adjacent the associated wrist, a transverse termination formed from said lengths of rod defining said free distal end of the track, and a stabilizer joining free ends of said lengths of rod adjacent to said proximal end, said transverse termination and said stabilizer being adapted to maintain the rod lengths in said spaced parallel orientation;

traction means adapted to be secured to the finger distal to the injured joint, the traction means having a free end adapted to be placed in tension so as to apply a distraction force to the injured joint;

a yoke adapted to support said traction means in tension with the traction means disposed between said parallel sides of the track, the yoke bridging both sides of the track and mounted to the track to slidingly engage the sides of the track so as to be movable along said arch guided by said sides;

and track securing means adapted to secure said track to a wrist.

28. A dynamic traction device for treating a finger having an injured joint, and cooperating with traction means adapted to be secured to the finger distal to the injured joint, the traction means having a free end adapted to be placed in tension so as to apply a distraction force to the injured joint, the device comprising:

an arcuate track having a pair of spaced parallel sides formed into an arch having a selected radius of curvature which exceeds the length of the injured finger, and which extends between a distal end spaced from the fingertip and a proximal end adjacent the associated wrist;

a yoke adapted to support said traction means in tension, the yoke bridging both sides of the track and mounted to the track to slidingly engage the sides of the track so as to be movable along said arch guided by said sides;

a tension adjuster traversing said yoke and adapted for translational movement therethrough, the tension adjuster comprising a threaded rod apertured at one end to receive spring biasing means connected to finger attachment means adapted to be secured to a finger at one end and adapted to apply said distraction force to the injured joint, the tension adjuster having adjustable stop means comprising a barrel nut of corresponding thread disposed on the rod with the yoke between the nut and the finger attachment means, the stop means being adapted to engage the yoke when said distraction force is applied, the relative position of the tension adjuster to the yoke defining the magnitude of the distraction force applied to an injured joint, and the other end of the rod being apertured to receive an annular loop through which a tensiometer may be inserted to measure the distraction force applied to an injured joint; and track securing means adapted to secure said track to a wrist.

29. A dynamic traction device for treating a finger having an injured joint, and cooperating with traction means adapted to be secured to the finger distal to the injured joint, the traction means having a free end adapted to be placed in tension so as to apply a distraction force to the injured joint, the device comprising:

an arcuate track having a pair of spaced parallel sides formed into an arch having a selected radius of curvature which exceeds the length of the injured finger, and which extends between a distal end spaced from the fingertip and a proximal end adjacent the associated wrist;

a yoke adapted to support said traction means in tension, the yoke bridging both sides of the track and mounted to the track to slidingly engage the sides of the track so as to be movable along said arch guided by said sides;

and track securing means adapted to secure said track to a wrist, the arcuate track having a planar termination adjacent said proximal end and the track securing means comprising a track receiving member traversed by said planar termination and adapted to allow translational movement of the planar termination therethrough, the track receiving member being adapted to adjust the relative longitudinal position of the planar termination in the track receiving member and thereby to position the centre of the arch so that it may lie on an injured joint, and the track receiving member being slidably mounted for translational movement across the wrist onto a supporting base and adapted to adjust the relative transverse position of the arcuate track to the base and thereby to position the arch over a finger with an injured joint.

30. A dynamic traction device for treating a finger having an injured joint, and cooperating with traction means adapted to be secured to the finger distal to the injured joint, the traction means having a free end adapted to be placed in tension so as to apply a distraction force to the injured joint, the device comprising:

an arcuate track formed into an arch having a selected radius of curvature which exceeds the length of the injured finger, and which extends between a distal end spaced from the fingertip and a proximal end adjacent the associated wrist;

a yoke adapted to support said traction means in tension, the yoke being mounted to the track to slidingly engage the track so as to be movable along said arch;

and track securing means adapted to secure said track to a wrist, the track securing means being slidably mounted for translational movement across the wrist onto a supporting base and adapted to adjust the relative transverse position of the arcuate track to the base and thereby to position the arch over a finger with an injured joint.

* * * * *